US00PP36134P3

(12) United States Plant Patent
VandenLangenberg et al.

(10) Patent No.: US PP36,134 P3
(45) Date of Patent: Sep. 24, 2024

(54) STRAWBERRY PLANT NAMED 'CBC015'

(50) Latin Name: ***Fragaria* x *ananassa***
Varietal Denomination: CBC015

(71) Applicant: Calfifornia Berry Cultivars, LLC, French Camp, CA (US)

(72) Inventors: Kyle M VandenLangenberg, Tracy, CA (US); Douglas V Shaw, Davis, CA (US)

(73) Assignee: California Berry Cutivars, LLC, French Camp, CA (US)

( * ) Notice: Subject to any disclaimer, the term of this patent is extended or adjusted under 35 U.S.C. 154(b) by 0 days.

(21) Appl. No.: 18/532,069

(22) Filed: Dec. 7, 2023

(65) Prior Publication Data

US 2024/0292768 P1 Aug. 29, 2024

Related U.S. Application Data

(60) Provisional application No. 63/448,642, filed on Feb. 27, 2023.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

| | | | |
|---|---|---|---|
| PP19,975 | P2 | 5/2009 | Shaw et al. |
| PP20,363 | P2 | 9/2009 | Chandler |
| PP26,708 | P3 | 5/2016 | Shaw et al. |
| PP26,709 | P3 | 5/2016 | Larson et al. |
| PP35,197 | P2 | 5/2023 | VandenLangenberg et al. |

OTHER PUBLICATIONS

Mercados Newsletter, Apr. 19, 2022, 3 pages https://revistamercados.com/eurosemillas-debemos-desarrollar-variedades-sostenibles-y-viables-economicamente/.
Mercados Newsletter, Aug. 26, 2022, 3 pages https://revistamercados.com/adelanto-y-cbc015-las-nuevas-variedades-de-fresa/.
Issuu article, Mar. 2022, 3 pages https://issuu-com.translate.goog/revistamercados/docs/mercados_159/s/15139803?_x_tr_sl=es&_x_tr_tl=en&_x_tr_hl=en&_x_tr_pto=sc.

*Primary Examiner* — Kent L Bell
(74) *Attorney, Agent, or Firm* — Phase M Legal

(57) ABSTRACT

A new and distinct cultivar of strawberry plant (*Fragaria* x *ananassa*) named 'CBC015' is presented here. This new short-day strawberry cultivar is characterized by moderate vigor plants which produce exceptionally large carly yields of attractive conical fruit. In addition, plants of 'CBC015' are resistant to *Macrophomina phaseolina*.

7 Drawing Sheets

Latin name of the genus and species of the plant claimed: Botanical classification: *Fragaria* x *ananassa*.

Variety denomination: The new strawberry variety denomination is 'CBC015'.

BACKGROUND OF THE INVENTION

This invention relates to a new and distinctive short-day type cultivar designated as 'CBC015'. The new cultivar was the result of a controlled cross performed in 2015 in Huelva, Spain between the cultivar 'Grenada' (U.S. Plant Pat. No. 26,708) and the unpatented cultivar 'Primoris'. 'CBC015' was first fruited at an experimental orchard near Oxnard, Calif. in 2016, where it was selected, originally designated 115.012-608, and propagated asexually by runners. Following selection and during testing, the plant of this selection was later designated 'CBC015'. Asexual propagules from this original source have been evaluated in Watsonville, Calif., in Oxnard, Calif., and to a limited extent in grower fields starting in 2020. The cultivar is stable and reproduces true to type in successive generations of asexual reproduction.

Comparison With Parents

The female parent 'Grenada' is a short-day cultivar that was selected for its overall high appearance score and large, firm fruit. Plants of 'Grenada' are smaller than 'CBC015'. The male parent 'Primoris' is a short-day cultivar that was selected for its high early season yield. Plants of 'Primoris' are larger in size than 'CBC015'.

SUMMARY OF THE INVENTION

'CBC015' is a short-day cultivar that produces fruit over an extended period when treated appropriately in arid, sub-tropical climates. When treated with appropriate planting regimes, 'CBC015' has larger fruit and produces individual plant yields greater than that of either parent. The following traits have been repeatedly observed over multiple testing years and locations and are determined to be unique characteristics of 'CBC015'. These characteristics in combination distinguish 'CBC015' as a new and distinct Strawberry plant:

1. Large sized plant.
2. Early flowering habit.

3. Exceptional fruit flavor.
4. Large to medium glossy red fruit.
5. Fruit is firm throughout the growing season.
6. Fruit postharvest longevity is good.
7. Excellent freezer crop.

1 The cultivar 'CBC015', when planted under appropriate conditions, is an early fruiting short-day cultivar with exceptionally high total yields. Fruit quality is good with excellent flavor. Early yield is of increased interest to fresh market strawberry sales companies as return prices on fruit volume are substantially higher. In addition to its early yield performance, 'CBC015' is resistant to *Macrophomina phaseolina*, the causal agent of charcoal rot.

BRIEF DESCRIPTION OF THE FIGURES

The accompanying color photographs, identified as FIGS. 1 through 7, show the appearance of typical specimens of the new strawberry cultivar designated 'CBC015'. These Figures depict the colors, as nearly true as it is reasonably possible given differences in color illustrations of this character. Accordingly, color in the photographs may differ slightly from the colors discussed in the botanical description.

DETAILED BOTANICAL DESCRIPTION OF THE PLANT

Figure 1:
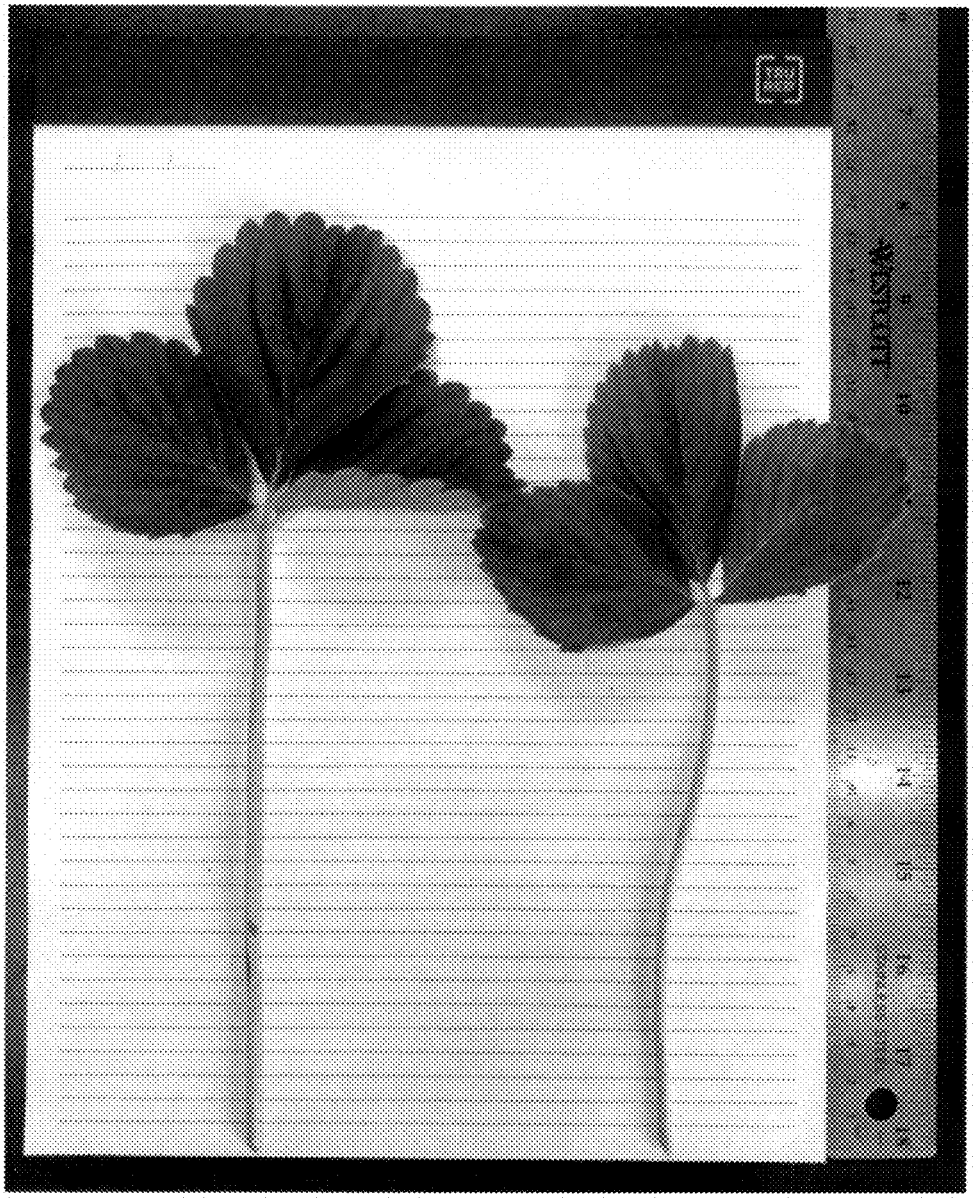
FIG. 1 shows a typical leaf and petiole structure.
Figure 2:
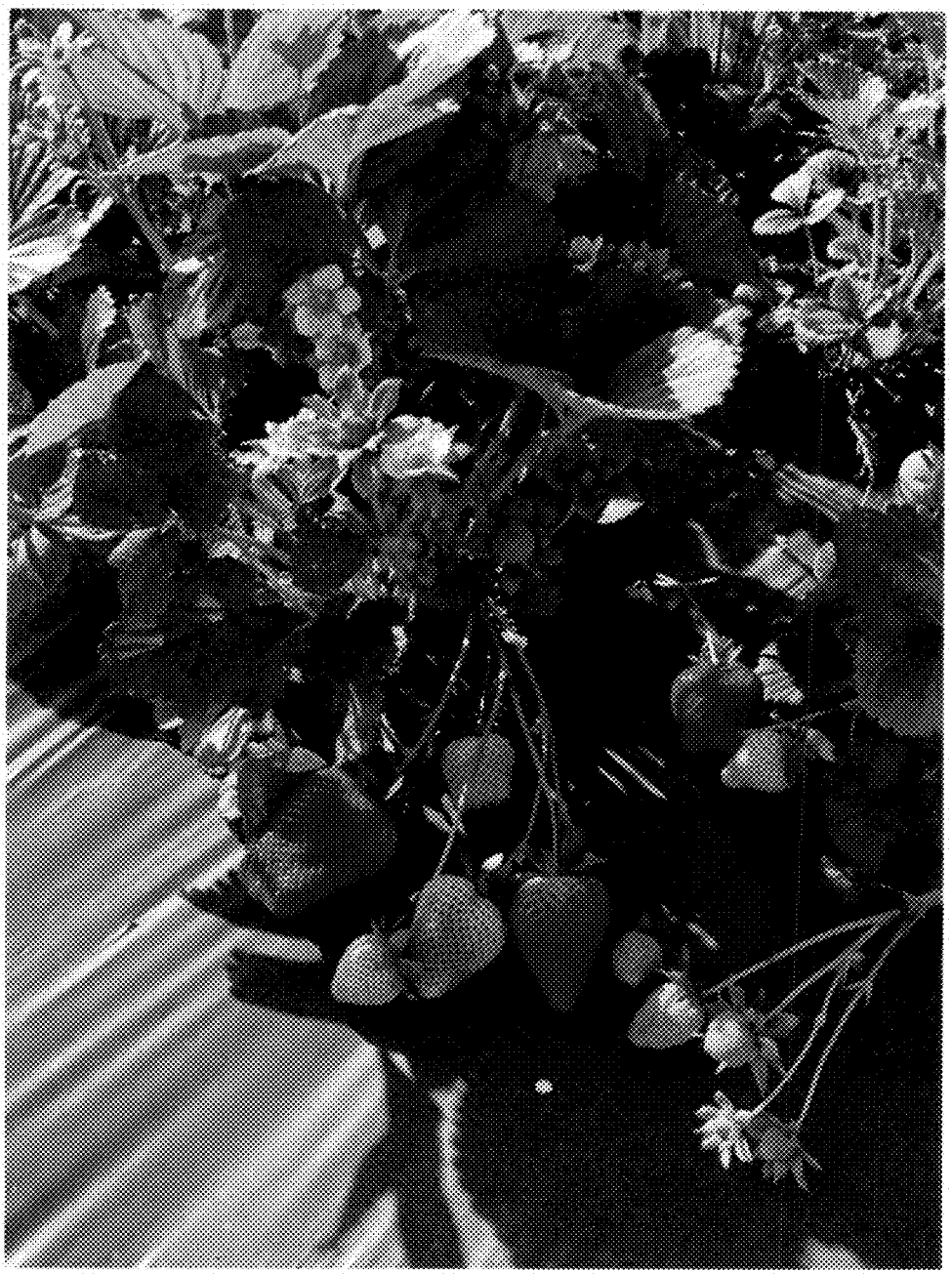
FIG. 2 shows a typical plant and fruit early season.
Figure 3:
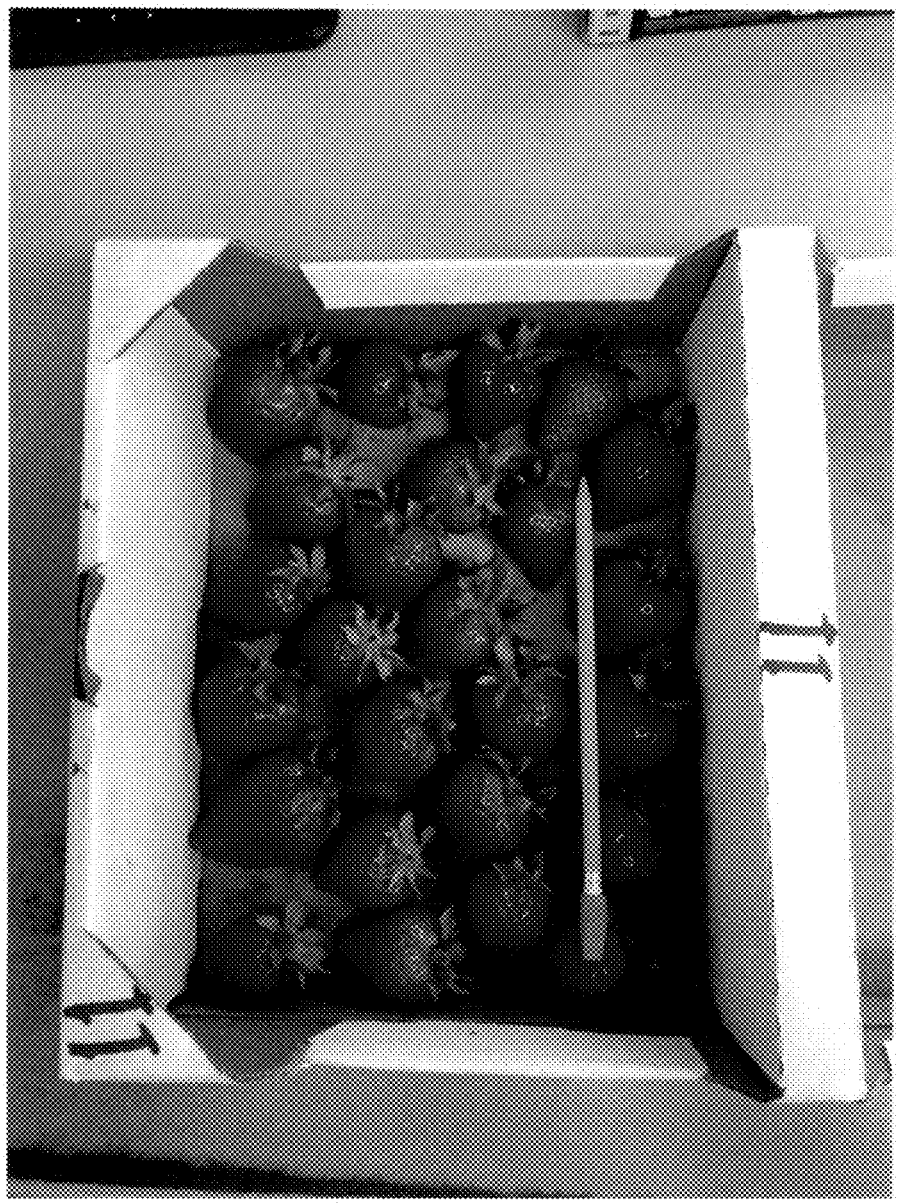
FIG. 3 shows typical fruit in a box in early season.
Figure 4:
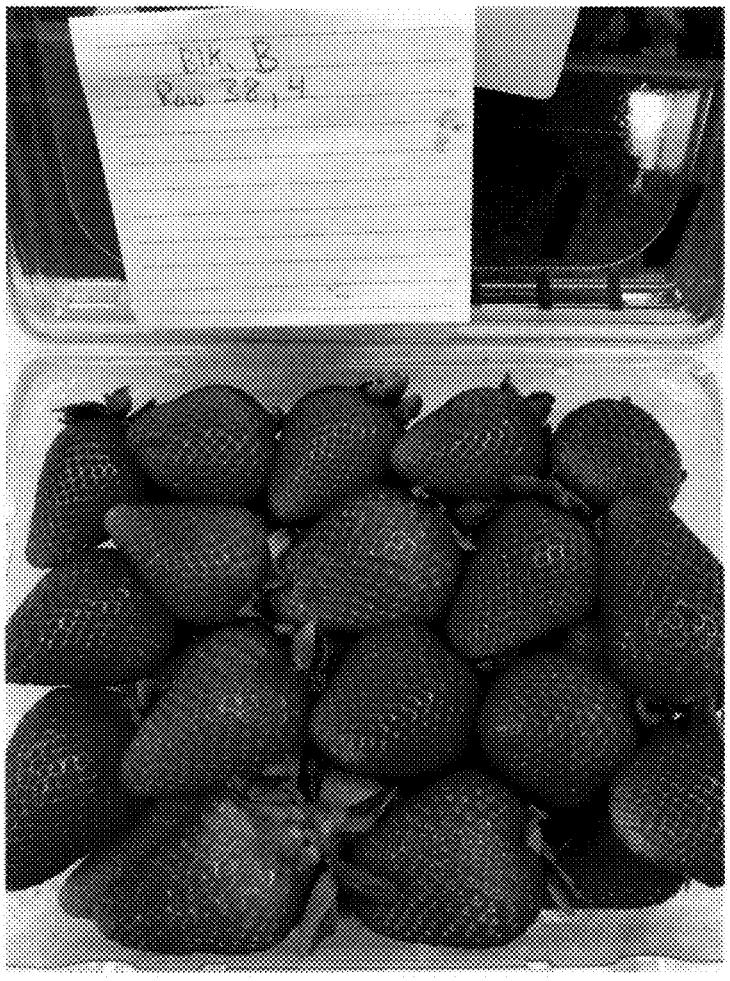
FIG. 4 shows typical fruit in a plastic box.
Figure 5:
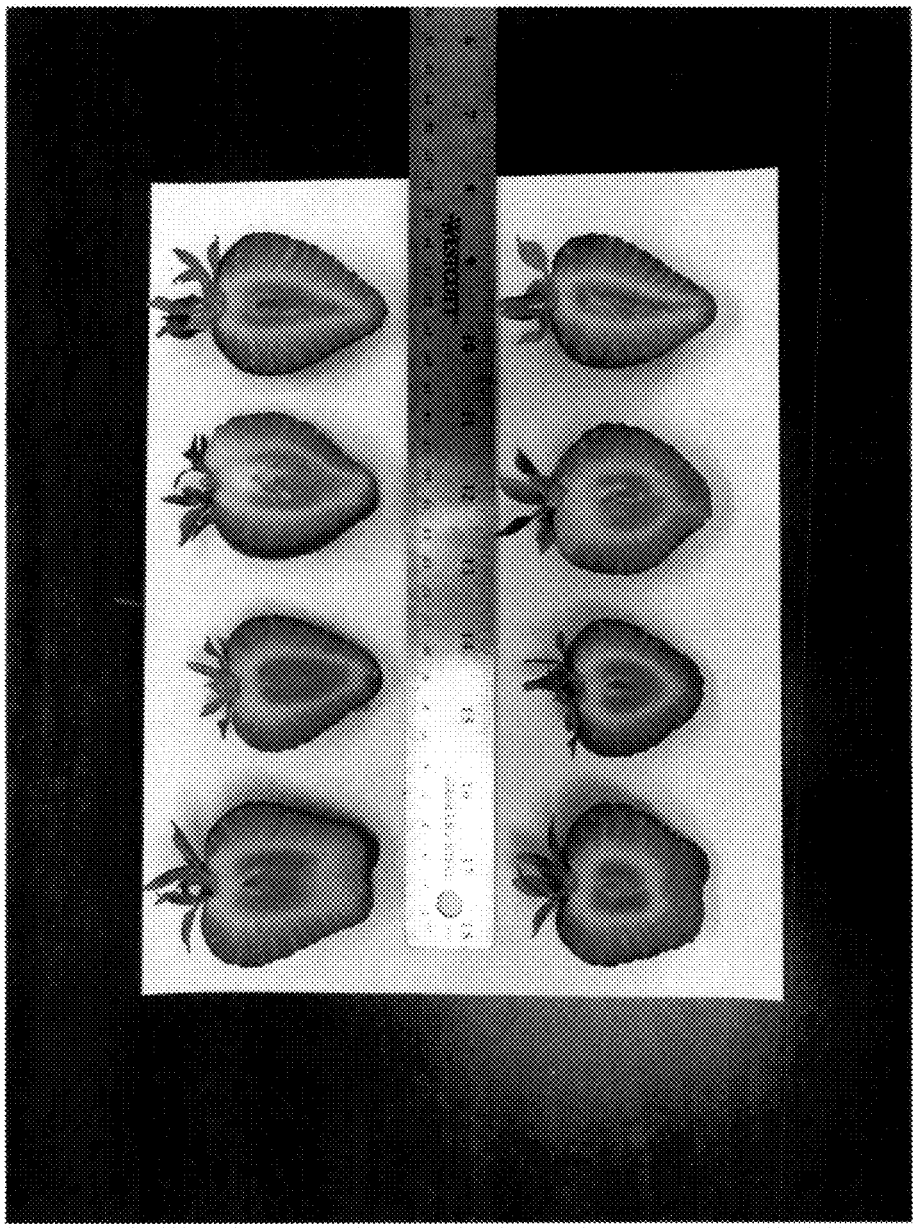
FIG. 5 shows a cross-section of representative fruit mid-season.
Figure 6:
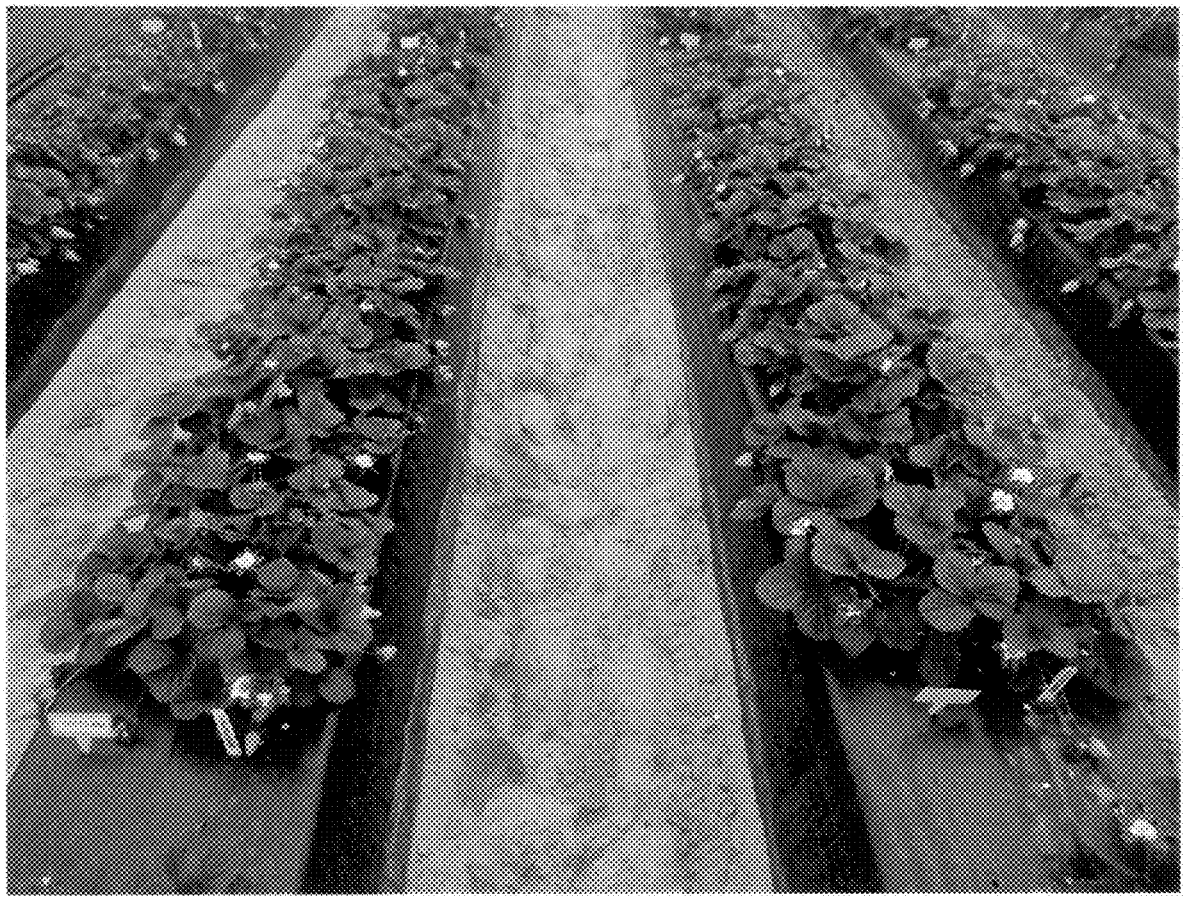
FIG. 6 shows a typical plot in the field of plants and fruit.
Figure 7:
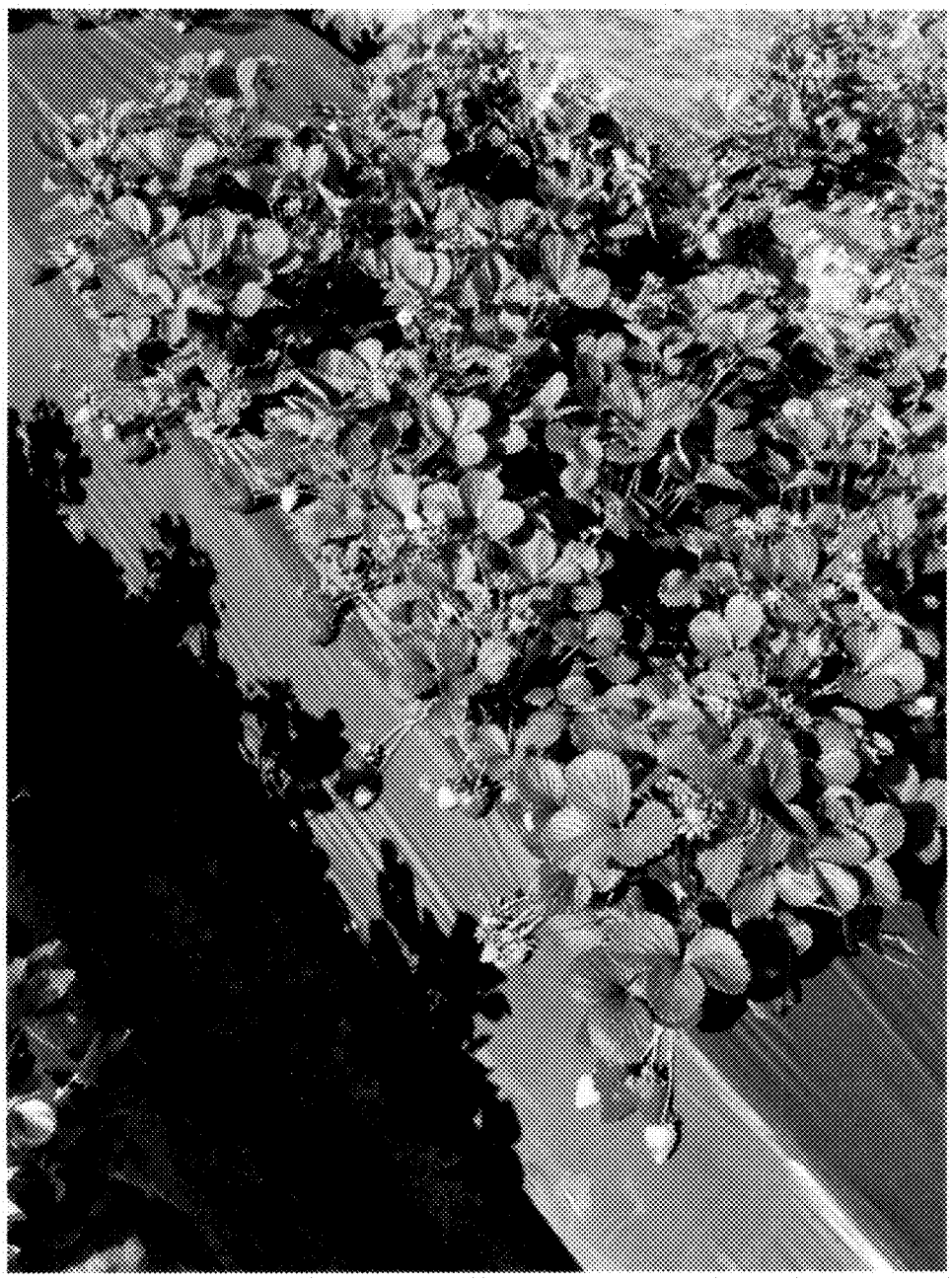
FIG. 7 shows a typical plot in the field of plants and fruit later in season.

'CBC015' is a new and distinct short-day cultivar of strawberry, genus and species *Fragaria* x *ananassa*. Plants of 'CBC015' do not bloom continuously in higher elevation plantings, and do not bloom in the heat of low elevation nursery locations such as French Camp, CA, consistent with other short-day varieties. The plants of the new cultivar have a moderate vigor and produce multiple crowns during the growing season. 'CBC015' exhibits several characteristics which are improvements over one or both of its parent varieties, and other cultivars known to the Inventors. These characteristics are compared with other cultivars in Table 2, 3, and 4.

The fruit size of 'CBC015' is moderately large, with a seasonal average of 35.5 g, slightly larger than its parents. The fruit size of 'CBC015' is generally good since it is not too large to be damaged in shipping containers, but not too small to allow for efficient picking and packing. The 'CBC015' fruit also hangs down on the shoulder of the bed later in the season, which makes for greater visibility and ease of picking. Storability of the fruit has not been measured but in informal observations the fruit retains good physical characteristics and appearance for several days after harvest at room temperature and up to at least a week in common refrigerator conditions of roughly 3° C.

'CBC015' produces mostly long conic fruit like its parent 'Grenada'. The fruit of 'CBC015' generally ripens evenly from the tip to the shoulders of the berry, resulting in a uniform red color over the whole fruit. In contrast, the fruit of 'Grenada' may have a blotchy color during the ripening process. The fruit of 'CBC015' can be exceptionally large early in the season, with weekly average of 60 grams per fruit.

The data set for 'CBC015' set forth below was collected in May 2023 from plants grown at a test plot in Oxnard, CA. Yield, size, and firmness data is either averaged over the entire 2022-2023 growing season or presented as monthly totals at the same location. Description data was collected on five-month-old plants.

The observed characteristics of 'CBC015' are set forth in Table 1, 2, 3, and 4 below. Color terminology is noted in accordance with Pantone Color Formula Guide GP1601A. The observed characteristics of 'CBC015' are also compared to known cultivars 'Fronteras' (U.S. Plant Pat. No. 26,709) and 'San Andreas' (U.S. Plant Pat. No. 19,975) in Table 2, 3, and 4. Table 5 sets forth the test results of DNA fingerprinting using eight SSR markers for 'CBC015' and for the recently patented variety 'CBC005' (U.S. Plant Pat. No. 35,197) for comparison.

TABLE 1

Detailed Description of Characteristics of 'CBC015'

| | |
|---|---|
| SPECIFICATION: | |
| Genus/Species | *Fragaria* X *ananassa* |
| Market Name | Strawberry |
| PARENTS: | |
| Female | 'Grenada' |
| Male | 'Primoris' |
| PLANT: | |
| Type | Short-day, non-everbearing |
| Growth Habit | Semi-upright |
| Foliage density | Moderate |
| Vigor | Moderate |
| Height | Average 29 cm; range 25-32 cm |
| Width | Average 21 cm; range 16-24 cm |
| Disease tolerance | Test plots have shown tolerance to *Macrophomina phaseolina* |
| Disease susceptibility | Susceptible to *Phytophthora cactorum* |
| LEAF: | |
| Width | 13 cm |
| Color | Adaxial surface: Pantone 574 C<br>Abaxial surface: Pantone 575 C |
| Pubescence | Slight density |
| Glossiness | Low |
| Variegation | Not present |
| TERMINAL LEAFLET | |
| Length | Average 71 mm; range 54-82 mm |
| Width | Average 57 mm; range 46-63 mm |
| Ratio (length/width) | 1.2 |
| Margins | Crenate to serrate |
| Leaflet shape | Obovate |
| Base shape | Cuneate |
| Cross-section shape | Concave |
| PETIOLE | |
| Pubescence | Medium density |
| Petiole color | Pantone 2300 C |
| Petiole length | Average 22 cm; range 17-30 cm |
| Petiole diameter | Average 3.7 mm; range 2.5-4.7 mm |
| STIPULE | |
| Anthocyanin coloration | Medium |
| Length | Average 24 mm; range 20-32 mm |
| Width | Average 9 mm, range 6-12 mm |

TABLE 1-continued

| Detailed Description of Characteristics of 'CBC015' | |
|---|---|
| INFLORESCENCE: | |
| Flowering time | Early |
| Position | Mostly at or above canopy |
| Petal arrangement | Slightly overlapping |
| Calyx size | Larger than corolla |
| Number of blooms | 15 |
| Length | 2.5 cm |
| Flower diameter | Average 30 mm; range 25-42 mm |
| Petal number | Average 5.5; range 5-6 |
| Petal length | Average 10 mm; range 8-12 mm |
| Petal width | Average 8.5 mm; range 8-10 mm |
| Petal color | Adaxial surface: Pantone 11-0601<br>Abaxial surface: Pantone 11-4300 |
| Ratio (length/width) | 1.2 |
| Calyx color | Adaxial surface: Pantone 2465 C<br>Abaxial surface: Pantone 2264 C |
| Stamens length | Average 25 mm; range 21-28 mm |
| PEDICEL | |
| Pubescence | Medium density |
| Length | Average 131 mm; range 114-153 mm |
| Width | Average 2.6 mm; range 1.5-3.8 mm |
| Ratio (length/width) | 50 |
| Color | Pantone 365 C |
| FRUIT: | |
| Bearing | Short-day, non-everbearing |
| Harvest Season | December 15$^{th}$ to June in Southern California |
| Length | Average 5 cm; range 4.5-5.5 cm |
| Width | Average 4 cm; range 3.5-4.5 cm |
| Individual fruit weight | Seasonal average: 35.5 g |
| Shape | Mostly conic |
| Achenes | Just below fruit surface |
| Glossiness | Medium/high |
| External color evenness | Even |
| External color | Pantone 1805 C |
| Internal color | Pantone 7417 C |
| Band at top without achenes | Narrow width |
| Fruit Yield | Grams per plant: 1222 g |
| Firmness | 0.69 kg/force |
| Achene color | Pantone 4211 C |

TABLE 2

Marketable yield of 'CBC015' compared to other known cultivars in Oxnard, CA during the 2022-2023 season.

| | Marketable yield (g/plant) | | | | | | |
|---|---|---|---|---|---|---|---|
| Cultivar | December | January | February | March | April | May | Total |
| 'Fronteras' | 2 | 180 | 194 | 356 | 319 | 478 | 1529 |
| 'San Andreas' | 24 | 135 | 84 | 202 | 324 | 247 | 1016 |
| 'CBC015' | 5 | 113 | 184 | 500 | 424 | 405 | 1628 |

TABLE 3

Size of 'CBC015' fruit compared to other known cultivars in Oxnard, CA during the 2021-2022 season.

| | Fruit size (g/fruit) | | | | | | |
|---|---|---|---|---|---|---|---|
| Cultivar | December | January | February | March | April | May | Average |
| 'Fronteras' | 49.0 | 46.2 | 43.8 | 30.6 | 24.7 | 23.8 | 36.3 |
| 'San Andreas' | 35.4 | 31.1 | 33.8 | 29.4 | 24.6 | 25.1 | 29.9 |
| 'CBC015' | 49.0 | 35.7 | 41.0 | 34.9 | 24.4 | 27.9 | 35.5 |

TABLE 4

Firmness of 'CBC015' compared to other known cultivars in Oxnard, CA during the 2021-2022 season.

| | Firmness (kg/force) | | | |
|---|---|---|---|---|
| Cultivar | March | April | May | Average |
| 'Fronteras' | 0.49 | 0.51 | 0.48 | 0.49 |
| 'San Andreas' | 0.61 | 0.62 | 0.58 | 0.60 |
| 'CBC015' | 0.67 | 0.62 | 0.59 | 0.63 |

TABLE 5

DNA finger printing results of eight SSR markers for 'CBC015' and 'CBC005'

| | Allelic Fingerprint Analysis | | | | | | | |
|---|---|---|---|---|---|---|---|---|
| Cultivar | M1 | M2 | M3 | M4 | M5 | M6 | M7 | M8 |
| 'CBC015' | 202, 214, 224, 229 | 259, 269, 271 | 182, 188, 190, 216 | 279, 289, 292 | 154<br>257, 264 | 238, 242, 251, | 121, 124, 130 | 215, 222, 228 |
| Cultivar | M1 | M2 | M3 | M4 | M5 | M6 | M7 | M8 |
| 'CBC005' | 212, 224, 229 | 259, 264, 269, 271, 275 | 190, 232 | 279, 289, | 154, 156 | 242, 257, 261 | 121, 130 | 215, 222, 228 |

We claim:

1. A new and distinct strawberry plant named 'CBC015' as described and illustrated herein.

* * * * *